United States Patent [19]

Bredwell

[11] 4,086,333

[45] Apr. 25, 1978

[54] METHOD OF ELIMINATING SEXUAL EXCITANTS FROM THE DISCHARGE OF A FEMALE ANIMAL IN ESTRUS

[76] Inventor: Claudia Bredwell, 15 W. 72nd St., New York, N.Y. 10023

[21] Appl. No.: 652,931

[22] Filed: Jan. 27, 1976

Related U.S. Application Data

[63] Continuation-in-part of Ser. No. 646,442, Jan. 5, 1976, abandoned.

[51] Int. Cl.² ............... A61K 9/02; A61K 31/20; A61K 31/22; A61K 33/40
[52] U.S. Cl. .................. 424/130; 128/270; 128/271; 128/285; 128/287; 128/288; 128/296; 424/DIG. 5; 424/DIG. 14; 424/28; 424/76; 424/148; 424/149
[58] Field of Search ............ 424/28, 76, 130, 148, 424/149, DIG. 14, DIG. 5; 128/263, 270, 271, 285, 288, 287, 296

[56] References Cited

U.S. PATENT DOCUMENTS

| | | | |
|---|---|---|---|
| 2,701,781 | 2/1955 | Guevara | 424/148 |
| 2,999,265 | 9/1961 | Duane et al. | 424/347 X |
| 3,067,743 | 12/1962 | Merton et al. | 128/270 |
| 3,123,521 | 3/1964 | Wentworth | 424/130 |
| 3,271,242 | 9/1966 | McNicholas | 424/76 X |
| 3,278,447 | 10/1966 | McNicholas | 424/149 X |
| 3,591,515 | 7/1971 | Lovely | 424/149 X |

*Primary Examiner*—Albert T. Meyers
*Assistant Examiner*—Vera C. Clarke
*Attorney, Agent, or Firm*—Blum, Moscovitz, Friedman & Kaplan

[57] ABSTRACT

The strong sexual excitants emitted by female animals when in heat and which serve to attract and arouse the male to mate are destroyed by treating with compounds containing chlorine dioxide in stable form. The compounds are non-irritating and are sufficiently effective when applied externally or internally so that a female in heat can be brought near a male of the same species without causing any appreciable change in the behavior of the male.

14 Claims, No Drawings

METHOD OF ELIMINATING SEXUAL EXCITANTS FROM THE DISCHARGE OF A FEMALE ANIMAL IN ESTRUS

CROSS-REFERENCE TO RELATED APPLICATION

This application is a continuation-in-part application of my co-pending application Ser. No. 646,442 filed Jan. 5, 1976 entitled METHOD OF ELIMINATING SEXUAL EXCITANTS FROM THE DISCHARGE OF A FEMALE ANIMAL IN ESTRUS, now abandoned.

BACKGROUND OF THE INVENTION

In those species of animals in which the females have a limited mating period known as estrus, and, particularly, where the animals are household pets, it frequently is desirable for one or more reasons to avoid the usual associated phenomena. Such phenomena, as when the animal is a dog, include the attracting of males from a fairly wide region as well as serious disturbance in the behavior of attracted males which are prevented from mating with the animal which is in season. Further, where the owner of the animal wishes to breed the female selectively, it becomes necessary to take the most rigorous precautions to keep unwanted males away. Another situation which is frequently extremely awkward is the introduction of a bitch in heat into a dog show. Thus, where male dogs are kenneled or housed near a bitch in season and not allowed access, the males may go off their feed or change in temperament so that they may not be shown to their best advantage, and the distress of the males may be evidenced as continuous whining and barking which can be extremely annoying. This last situation could result in a serious loss in income and prestige to the owner of the dog since the owner might have planned to show the dog with a view to winning an award.

In view of the various difficulties attendant on estrus in an animal when it is desired to control or prevent mating, it would obviously be desirable to be able to eliminate or overcome the effects of the sexual excitants emitted by the animal. Various attempts have been made, mostly along the line of the use of masking odors. However, such attempts have not been particularly successful largely because of the fact that nature has designed the olfactory nerves of the males of the various species so that they are extremely competent at detecting the presence of even a few molecules of the excitant in the air that they breathe.

Attempts to eliminate the excitant by feeding specific reagents to the animal have also been made, but these have not been successful. The present invention deals with a method of safely and completely eliminating the excitant in a manner which can be carried out by the dog's owner and which does not require the services of a veterinarian.

SUMMARY OF THE INVENTION

Chlorine dioxide, a strong oxidizing agent, can be stabilized by addition to a number of compounds. Such compounds are sodium carbonate peroxide and sodium perborate. The compounds can be applied in solution by spraying or by swabbing or similar means to the genital region of an animal in heat. The stabilized chlorine dioxide compound destroys the sexual excitant completely. Moreover, no odor of any kind is generated in the process.

The stabilized compound can be applied as an ointment to the exterior of the animal, as a vaginal douche or, in solid form, contained in a suppository inserted into the vagina of the animal. A solution of the compound has maximum effectiveness at a pH of 3.5 to 4.5. The preferred compound is the sodium carbonate peroxide addition product. Solutions of the stabilized compound are effective at concentrations of chlorine dioxide over the range from 50 ppm to upward of 60,000 ppm.

The pH value of a solution saturated with the addition compound of chlorine dioxide and sodium carbonate peroxide is about 9. The compound is effective, even at this pH, when sprayed on the genital region of a bitch, possibly due to the fact that the vaginal discharge of the bitch is acidic. Daily, or more frequent, applications are recommended for the duration of the estrus period in most cases.

Accordingly, an object of the present invention is a method of eliminating sexual excitants from the characteristic genital discharge of an animal in heat.

Another object of the present invention is a method of preventing sexual excitation of male animals in the vicinity of a female animal of the same species when the female animal is in estrus.

A further object of the present invention is a method usable by pet owners for eliminating sexual excitants from the discharges of their pets when in heat, the elimination being sufficiently effective so that no nearby males are attracted or disturbed.

An important object of the present invention is to make it possible to exhibit a bitch in heat at a show without causing disturbance among the male animals in the show.

A significant object of the present invention is a suppository which can be inserted into the vagina of an animal in heat for the purpose of reacting with and destroying sexual excitants emitted by the animal.

DESCRIPTION OF THE PREFERRED EMBODIMENTS

The manufacture of stabilized chlorine dioxide effective for destroying or eliminating sexual excitants emitted by female animals in estrus, is described in U.S. Pat. Nos. 2,701,781 and 3,123,521. The earlier patent describes the stabilization of chlorine dioxide with sodium perborate, and the later patent describes the stabilization of chlorine dioxide with sodium carbonate peroxide, this latter compound having the approximate formula $2Na_2CO_3 \cdot 3H_2O_2$. The peroxide addition product can be dried to a solid or can be brought to a concentration of about 63,000 ppm based on the available $ClO_2$.

It is believed that the perborate and percarbonate addition complexes with $ClO_2$ function by oxidizing the excitant. It is also possible that chlorination may take place. At any rate, it appears that the sexual excitant is altered sufficiently so that it is no longer recognized by the male of the corresponding species as a signal that a female in heat of the same species is in the vicinity.

The manufacture of the carbonate peroxide addition product is carried out by bubbling chlorine dioxide gas through a solution containing sodium carbonate peroxide at a concentration of about 12%. The product can contain up to about 63,000 ppm of chlorine dioxide. As first prepared, the pH of the solution is about 6.2. The pH rises to about 8.6 during storage due to the release of carbonic acid from solution.

When diluted 1:10 the solution is non-toxic when fed by stomach trocar. Also, it is non-toxic and non-irritating to mucous tissue at full strength. Accordingly, it is completely safe to apply by spraying of a solution and by insertion into a body cavity.

The effectiveness of the compound can be illustrated by consideration of an example of its use in connection with a female dog in heat. As is well known, when a bitch is in heat, glands near and in the vagina secrete a sexual excitant. In addition, the bitch raises its tail in a gesture termed "flagging" and arches its back in a characteristic fashion, the arched back being convenient for receiving the male in coitus. A number of males in succession were led into the presence of the bitch. It was apparent in each case that the male noticed the characteristic flagging and back-arching and was somewhat puzzled about the absence of the characteristic excitant. After a short interval, each male lost interest in the bitch and followed the instructions of its trainer.

As aforenoted, the solution is effective over a wide range of concentrations. In fact, concentrations as low as 50 ppm have an effect. However, a preferred range for application by spray or swabbing is from 500 ppm to the maximum concentration possible, namely about 63,000 ppm. Most conveniently, the solution should be applied at a concentration of 2,000 ppm.

The effect of the application or treatment usually lasts for about 24 hours, and it is advised that where suppression of the excitant is desired for a longer period than 24 hours, that the application of the stabilized compound be repeated at this frequency. Naturally, if a weaker solution is used, the treatment should be repeated more frequently.

In a breed where the discharge is abnormally great, a pad of the so-called sanitary napkin type, consisting of an absorbent material impregnated with the solution may be used. It may be necessary to change the pad as frequently as six or more times per day, and spraying of the genital region more frequently than the usual once in 24 hours is then advisable. The pad may be allowed to dry before use, or may be charged directly with the powder, either as such or in combination with sufficient acid to adjust the pH to 3.5 – 4.5.

Another means for controlling the discharge is a tampon charged with a stabilized chlorine dioxide compound, the tampon to be inserted in the vagina of the animal, and replaced as frequently as needed. A further control method is by the use of panties, to be fitted to the genital region of the animal, at least the crotch of the panties being charged with the compound. Again, acid may be added to the compound charged into the tampon or panties to bring the pH to the optimum range.

Where a tampon is used, it may be mounted at its outer end to a plate or shield which remains at the entrance of the animal's vagina and blocks entry by the male. The inner surface of the plate or shield may be provided with an adhesive for retaining the plate or shield assembled to the tampon in position on the animal.

The stabilized compound is effective as a douche, the quantity inserted being regulated in accordance with the breed or species of animal. Also, the treatment can be effected by incorporating the solid in a suppository and inserting it into the vagina of the animal.

Although the compound is most effective at a pH of 3.5 to 4.5, it has been found that it can be used practically without adjustment of the pH. It is possible that this is due to natural acidity in the discharge of the animal. Nevertheless, for maximum effectiveness, the pH should be adjusted. The adjustment can be carried out using any convenient acid which is pharmaceutically acceptable. For solutions, acetic acid, phosphoric acid and hydrochloric acid can be used. Phosphoric acid is particularly appropriate because of the fact that it produces no odor. Where the solid compound is to be used, as in a suppository, it can be admixed with a quantity of a solid acid, the quantity of solid acid being such that when the addition compound and the acid go into solution in the vaginal fluid, the pH will lie between about 3.5 and 4.5. Examples of suitable solid acids are citric acid and lactic acid.

The preferred stabilized form of chlorine dioxide is in the addition compound with sodium carbonate peroxide, due to the fact that its toxicity is so low and to the fact that it is non-irritating to mucous membrane. Moreover, its stability during storage is excellent, whether stored as a solution or as a solid. The solution is effective over a wide range of concentrations and can readily be prepared from a stock solution containing 50,000 ppm to bring it to a concentration of 2,000 ppm to 5,000 ppm. The efficacy of the solution is improved by adding a wetting agent, any of the common wetting agents being suitable.

It will thus be seen that the objects set forth above, among those made apparent from the preceding description are efficiently attained and since certain changes may be made in carrying out the above method and in the composition set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method of eliminating sexual excitants emitted by a female animal in estrus, comprising the step of topically treating with an effective amount of a compound incorporating stabilized chlorine dioxide that region of said animal where said excitant is present, said compound being selected from the group consisting of those formed by the reaction of chlorine dioxide with sodium carbonate peroxide and chlorine dioxide with sodium perborate.

2. The method as defined in claim 1, wherein said compound is that formed by reaction of chlorine dioxide with sodium carbonate peroxide and said compound is in solution in water in an amount such that the solution formed is effective when said region is topically treated.

3. The method as defined in claim 2, wherein the concentration of chlorine dioxide in stabilized form in said solution lies between about 500 ppm and about 63,000 ppm.

4. The method as defined in claim 2, wherein the concentration of chlorine dioxide in stabilized form in said solution lies between about 2,000 ppm and 5,000 ppm.

5. The method as defined in claim 2, wherein said animal is topically treated with said solution by spraying the genital region of said animal with said solution.

6. The method as defined in claim 2, wherein said animal is topically treated with said solution by introducing the same into the vagina of said animal.

7. The method as defined in claim 2, wherein said solution is adjusted to a pH of 3.5 to 4.5 with a soluble, pharmaceutically acceptable acid.

8. The method as defined in claim 2, wherein said solution also contains a wetting agent.

9. The method as defined in claim 1, wherein said treatment is carried out with sufficient frequency to prevent continuously the escape of said sexual excitant over the duration of a selected period of time.

10. The method as defined in claim 1, wherein said compound in solid form is admixed in a suppository with a solid, pharmaceutically acceptable acid in a quantity such that when said admixture is dissolved in vaginal fluid the pH will be between 3.5 and 4.5 and said treatment includes the step of inserting an effective amount of said admixture in said suppository into the vagina of said animal.

11. The method as defined in claim 10, wherein said compound is the reaction product of sodium carbonate peroxide with chlorine dioxide.

12. The method as defined in claim 10, wherein said compound is the reaction product of sodium perborate with chlorine dioxide.

13. The method as defined in claim 1, wherein said animal is a bitch.

14. A suppository composition suitable for eliminating a sexual excitant emitted by an animal in estrus, comprising the admixture of an effective amount of a solid reaction product of chlorine dioxide with a compound selected from the group consisting of sodium carbonate peroxide and sodium perborate, and a pharmaceutically acceptable solid acid, the ratio of said reaction product to said solid acid being such that when said admixture is dissolved in vaginal fluid the pH will be between about 3.5 and 4.5.

* * * * *